United States Patent [19]
Ashby et al.

[11] Patent Number: 5,413,605
[45] Date of Patent: May 9, 1995

[54] TIBIAL ELEMENT FOR A REPLACEMENT KNEE PROSTHESIS

[75] Inventors: Alan M. Ashby; Peter Lawes, both of Maidenhead, England

[73] Assignee: Howmedica International, Inc., Shannon, Ireland

[21] Appl. No.: 754

[22] Filed: Jan. 5, 1993

[30] Foreign Application Priority Data

Jan. 21, 1992 [GB] United Kingdom ............... 9201231

[51] Int. Cl.⁶ ............................................. A61F 2/38
[52] U.S. Cl. ........................................ 623/20; 623/18
[58] Field of Search ............... 623/18, 20, 16, 66, 623/19

[56] References Cited

U.S. PATENT DOCUMENTS

| | | | |
|---|---|---|---|
| 4,016,606 | 4/1977 | Murray et al. | 623/20 |
| 4,578,081 | 3/1986 | Harder et al. | 623/22 |
| 4,759,767 | 7/1988 | Lacey | 623/20 |
| 4,790,854 | 12/1988 | Harder et al. | 623/20 |
| 4,822,362 | 4/1989 | Walker et al. | 623/20 |
| 4,822,362 | 4/1989 | Walker et al. | 623/20 |
| 4,936,853 | 6/1990 | Fabian et al. | 623/20 |
| 4,938,769 | 7/1990 | Shaw | 623/20 |
| 4,944,757 | 7/1990 | Martinez et al. | 623/20 |
| 4,963,152 | 10/1990 | Hoffman et al. | 623/20 |

FOREIGN PATENT DOCUMENTS

| | | | |
|---|---|---|---|
| 2663536 | 12/1991 | France | 623/20 |
| 2674123 | 9/1992 | France | 623/20 |
| 2678824 | 1/1993 | France | 623/20 |
| 2744710 | 4/1979 | Germany | 623/20 |

*Primary Examiner*—David Isabella
*Assistant Examiner*—Debra S. Brittingham
*Attorney, Agent, or Firm*—Peter C. Richardson; Lawrence C. Akers; Raymond W. Augustin

[57] ABSTRACT

A prosthetic tibial component has a tibial tray having an underside for engaging a prepared tibial plateau. The tibial component has a stem having a tapered connection at one end. The stem has a non-symmetrically shaped bone engagement element extending therefrom. The tray includes a tapered connection element for mating with the tapered connection element on the stem. The tray includes an alignment element for locating and engaging the bone engagement element on the stem to locate the stem at a predetermined position relative to the tibial plateau.

10 Claims, 4 Drawing Sheets

TIBIAL ELEMENT FOR A REPLACEMENT KNEE PROSTHESIS

BACKGROUND OF THE INVENTION

1. Field of the Invention

This invention relates to a tibial element for a replacement knee prosthesis. More particularly, the invention relates to a modular tibial element in which the stem may be placed in a predetermined position with respect to a separate tibial tray.

2. Description of the Prior Art

Tibial elements for replacement knee prostheses are known which are provided with one or more selectable alternative stems which can be selected by the surgeon to meet the requirements of the patient. In devices of this kind, the selected stem is usually threaded into or onto the tibial tray and due to the stems themselves usually being relatively circularly symmetrical about a longitudinal axis, their angular position relative to the tibial tray is immaterial. For example, see U.S. Pat. No. 4,822,366. There are, however, advantages in being able to provide stems which are non-symmetrical, but in order to do this it is necessary to be able to locate them in relation to the tibial tray so that the desired relative configuration is obtained. The present invention is intended to provide a construction to allow this.

U.S. Pat. No. 4,936,853 relates to a modular knee prosthesis in which a selected stem is located into a tibial tray by means of a self-locking morse taper. A number of alternative modular stems are described which may be provided with flutes or have radially projecting flanges. Such flanges are shown in U.S. Pat. Nos. 4,822,362 and 4,938,769.

In constructions of the type set forth above, the surgeon selects the appropriate stem for the patient concerned at the time of the operation and the stem is then assembled to the tray in the surgery. Difficulties arise, however, during assembly due to the tendency for the stem to rotate in the tapered socket in the tray when the locking device, usually a pin or bolt, is tightened. It is often necessary for there to be accurate alignment between the cross-sectional shape of the stem and the configuration of the tray, and this tends to be lost during tightening. This misalignment is particularly acute if the lower portion of the tray has a shaped engagement feature intended for engagement with the condylar area of the tibia of the user. The present invention is intended to overcome the disadvantage set out above.

U.S. Pat. Nos. 4,578,081 and 4,790,854 disclose one method of aligning a morse taper stem connection, but not in relation to a tibial tray.

SUMMARY OF THE INVENTION

It is an object of the invention to provide a modular tibial element in which the modular stem can be located at a predetermined position with respect to the modular tibial tray.

According to the present invention, a tibial element for a replacement knee prosthesis comprises a tibial tray provided with one or more polyethylene bearing components. The lower portion of the tray has a shaped engagement feature intended for engaging with the proximal subcondylar area of the tibia of the user, and a stem which can be attached to the tray by a tapered, preferably conically tapered, spigot and socket construction. An element is provided for locating the stem in a predetermined angular position in relation to the shaped engagement feature on the tray.

Thus, the locating means can be arranged to act to prevent relative angular movement in the direction of rotation if means for drawing the spigot or trunion and socket connection together in the form of a screw are used. In a preferred embodiment the locating means includes an abutment on the engagement feature which acts on a location portion provided on the stem. In a preferred embodiment the shaped engagement feature comprises two projections which extend radially outwardly from the spigot and socket connection and these may be in the form of angled fins.

Two abutments can be provided, one on each of the projections, and at a position spaced radially away from the spigot and socket connection. The stem can be provided with a substantially radially outwardly projecting flange or flanges, and thus two flanges can be aligned with said radially outwardly extending projections on the tray which carry the abutments. Preferably the stem is of substantially cruciform cross-section to provide four radially extending wings.

The conically tapered spigot and socket connection can rely on applied end pressure to hold it in position, the locating means acting to ensure that it is accurately located in a predetermined angular position. However, if desired, means my be included for drawing the spigot and socket connection together and maintaining it in position. The locating means acts to prevent any undesired angular rotation between the parts during tightening, or during the implanted life of the product if overload occurs or fixation breakdown occurs. A number of alternative stems can be provided with each tray so that there is a modular assembly.

The bearing surface or surfaces can be provided on a bearing component or components secured to the upper portion of the tray, and these can be of the form set forth in the Applicant's co-pending European Patent Application No. 89307478.1 (Publication No. 0 353 921). The lower surface of the tray is preferably provided with an ingrowth surface to allow bone to interlock therewith.

If desired, openings can be provided in the tray to receive screws to secure the initial fixture of the tray into the bone stock.

While several examples of the present invention have been described, it is obvious that many changes and modifications may be made thereunto, without departing from the spirit and scope of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
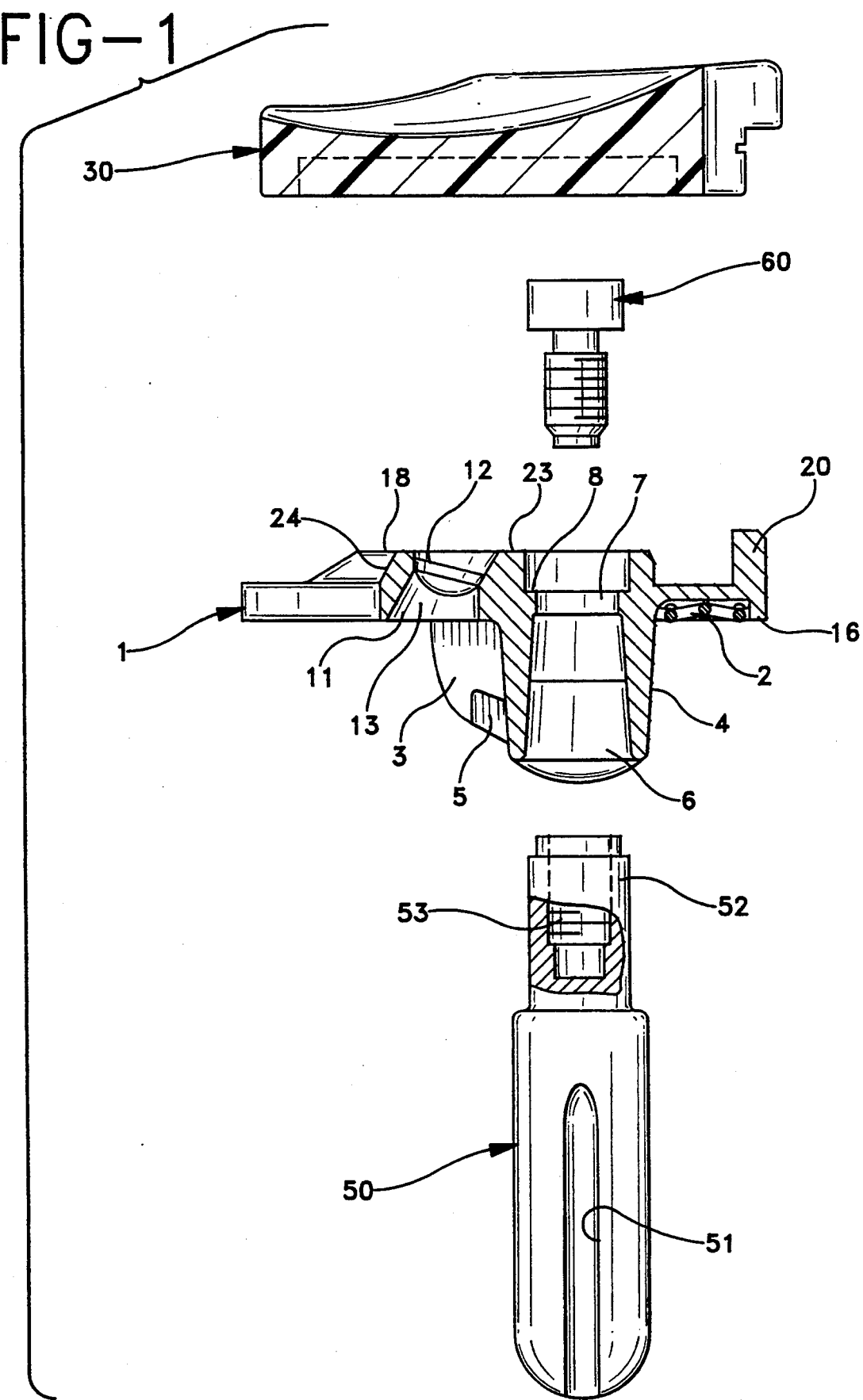
FIG. 1 is an exploded pad-sectional side elevation of the components of a modular construction of a tibial element ready for assembly.
Figure 2:
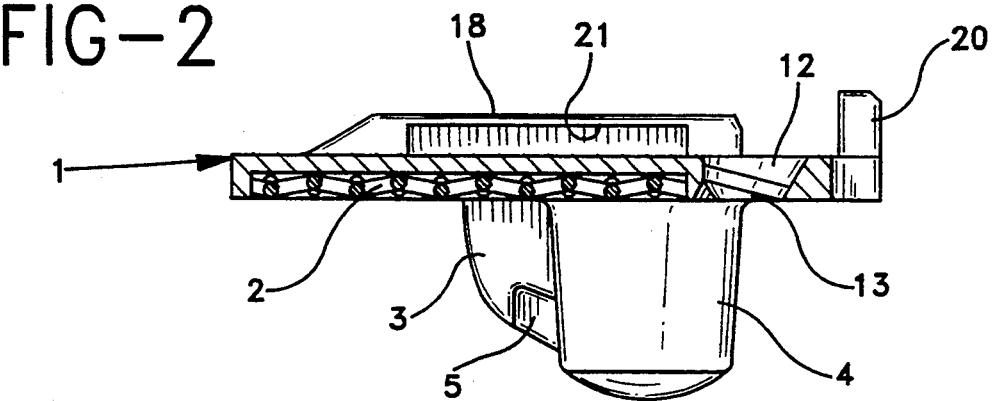
FIG. 2 is a cross-sectional side elevation of a tibial tray embodying the invention taken on the line II—II of FIG. 5 with sectioned web (not shown)

The drawings show a modular construction for a tibial element for a replacement knee prosthesis according to the present invention which includes a tibial tray and a number of alternative stems. FIG. 1 shows a tibial tray 1 which is a cast metallic construction, the lower surface of the tray is provided with an integrally cast ingrowth surface 2 which is more clearly shown in FIGS. 2, 3 and 4. This ingrowth surface can be of any known kind of ingrowth surface which can be either integrally cast or sintered, diffusion bonded or fabricated to it to allow the bone to interlock when the tray has been fitted. Alternatively, the surface could be roughened or textured to allow for good attachment with bone cement.

The lower portion of tray 1 is provided with a shaped engagement feature in the form of two fins 3 provided which extend outwardly from a central downwardly extending boss 4 and into the condylar area of the tibia when fitted and these fins allow for good torsional stability with minimal invasion of bone stock. On each fin there is a small recess 5 which provides an abutment adjacent the boss 4, the purpose of which will be described hereafter.

The boss 4 has a bore 6, the walls of which are tapered to provide a Morse taper, and the upper end of the bore extends into the top surface of the tray by a cylindrical portion 7, the upper end of which is counterbored to provide a projecting flange 8.

Figure 3:
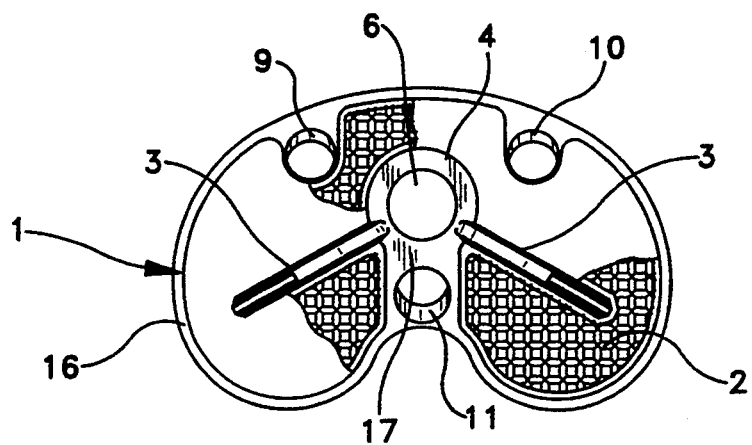
FIG. 3 is a plan view from beneath the tibial tray shown in FIG. 2, but to a smaller scale.
Figure 4:
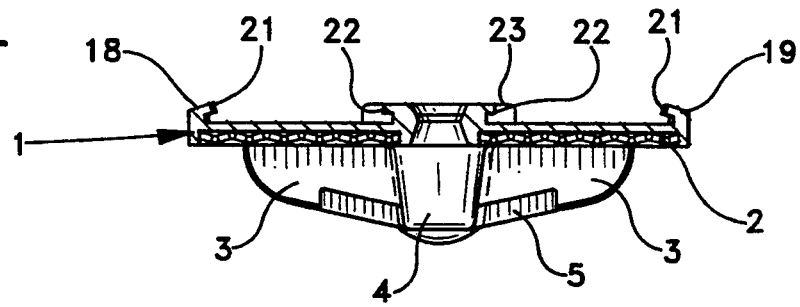
FIG. 4 is a partial cross-sectional view on the line IV—IV of FIG. 5 with the webs not sectioned, but shown complete.
Figure 5:
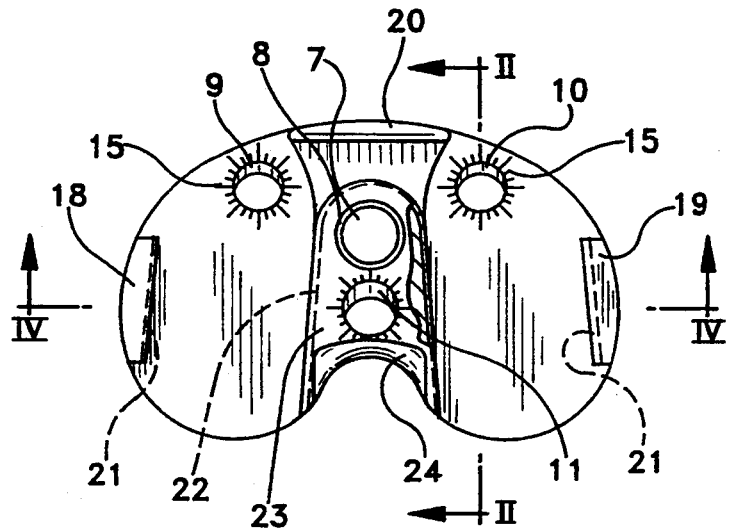
FIG. 5 is a plan view from above the tibial tray shown in FIG. 2.

The tray is provided with three screw holes 9, 10, 11 which are most clearly shown in FIGS. 3 and 5. These screw holes allow for the placement of cortical or cancellous bone screws or alternatively, bone screws which connect to resorbable fasteners to allow the more secure initial fixation of the tray into the bone stock. When a cemented tray is to be used, these screw holes will not be provided. The screw holes 9, 10, 11 are arranged in a configuration which is thought to have biomechanical advantages. The posterior screw hole 11 in the central intercondylar area allows for a cortical or cancellous screw to be placed into the posterior bone stock of the tibia. The two anterior screw holes 9 and 10 allow for the angulation of screws down into the cancellous bone stock or alternatively, to the cortex in a number of possible areas laterally and posteriorly.

Figure 12:
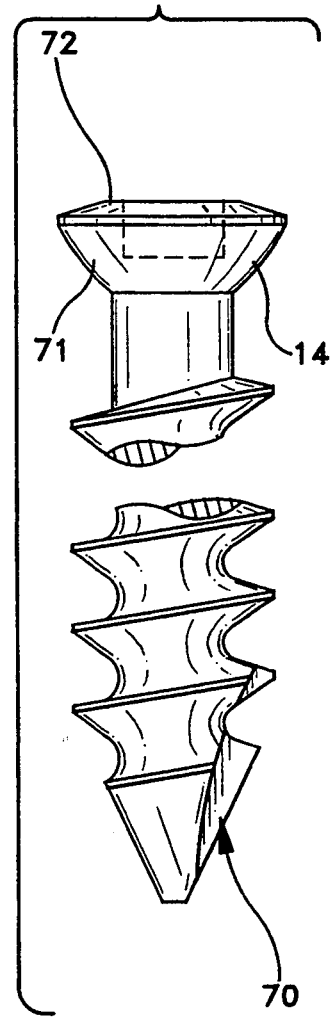
FIG. 12 is a side elevation of a retaining screw for use with the invention.

These screws must be placed very carefully if they are placed into the anterior areas of the tibia due to the very thin skin coverage of the anterior cortex. As will be seen most clearly from FIGS. 1 and 2, the upper end 12 of these screw holes is spherical and the lower end 13 conical. This allows for some angulation chosen by the surgeon at the time of insertion of the screws. A typical screw is shown in FIG. 12, the head 70 of which has a shallow part-spherical underside 71, 14 to cooperate with the spherical shape of the upper end 12 of the holes.

The upper surface 72 of the head 70 is of shallow part-conical form. This ensures that there is accurate conformity between the screw and its seat in all positions of angular operation, and the conical form of the top drive surface of the screw ensures the minimal clearance so that it does not foul with the plastic bearing component 30 when it is subsequently introduced into the tibial tray.

The particular combination of locations of screw holes and fins on the tray allow them to be used simultaneously since the screws avoid the other fixation elements. It will be noted that none of the holes 9, 10, 11 are in a position which may induce stress intensities in the overlying bearing component 30. Such stresses must be avoided in areas of high load support, as for example in the center of the tibial condyles.

The top surface of the tray is marked with compass lines 15 around the holes 9 and 10, which can be used by the surgeon when he pre-drills the bone for the insertion of the screws, allowing for more accurate placement. These are usable even when drilling is done free hand or when a directing instrument is used to more accurately locate the screws. The overall shape of the tibial tray 1 is designed to match as closely as possible, with a symmetric design, the cross-sectional face of the tibial bone when it is resected.

The underside surface of the tray 1 incorporates a boundary wall structure 16 and a built up area 17 in the intercondylar posterior zone. The boundary wall 16 reinforces the tibial tray from a flexural strength point of view. The solid area 17 in the posterior intercondylar area is to accommodate the posterior screw's passage through the hole 11, but also serves to reinforce the tray against fracture which, in some previous designs, has occurred in this area since it is subjected to the most extreme loads when offset bending of the tibial tray occurs.

The upper part of the tibial tray 1 has a number of male features which serve the function of locating the snap fit bearing elements 30, to be described, and also allows for the insertion of the fixing screw 60 for the modular stem 50, also to be described. Lugs 18 and 19, which are the medial and lateral extremes of the tray, and an anterior lug 20 locate the bearing components 30. Each bearing component 30 is held into the tray by a lip capture 21 on the extreme lateral or medial lug and a snap fit hook retention 22 into the rim of an intercondylar eminence structure 23.

Figure 9:
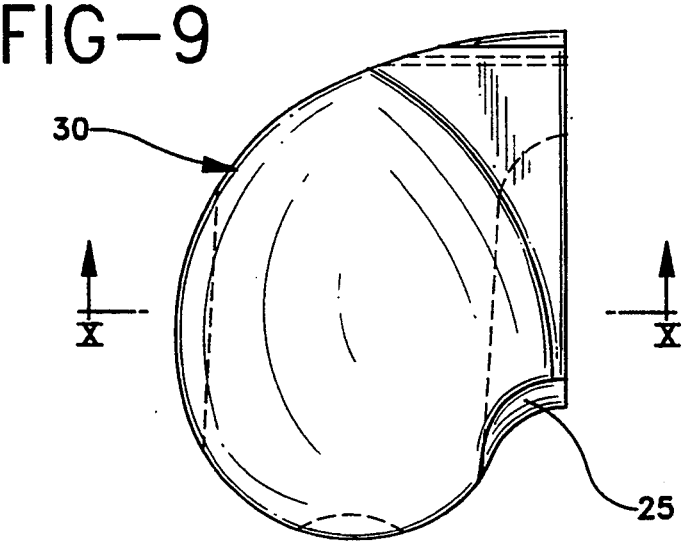
FIG. 9 is a plan view from above a bearing component for use with the invention.
Figure 10:
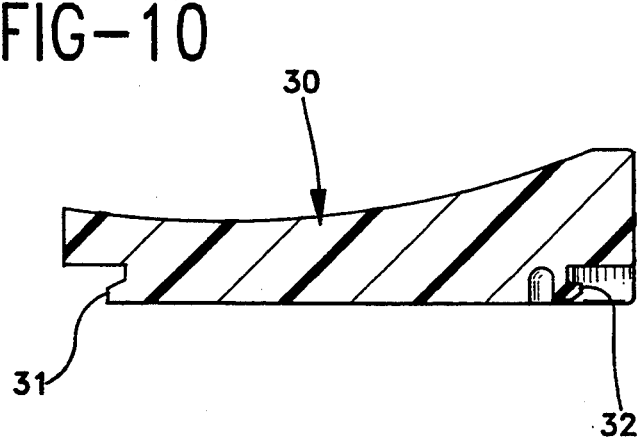
FIG. 10 is a cross-sectional view on the line X—X of FIG. 9.
Figure 11:
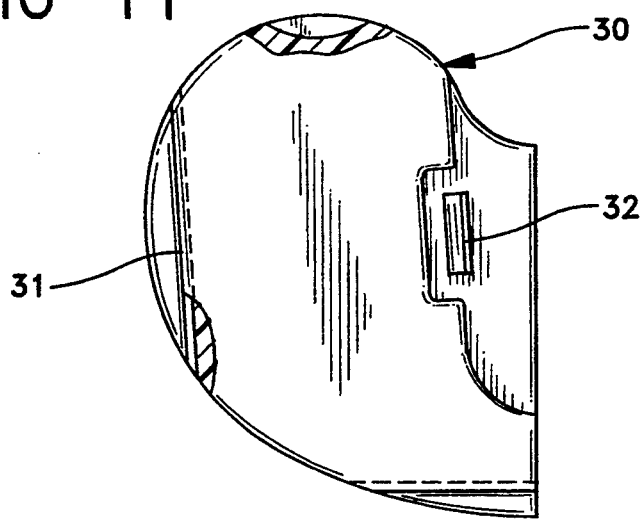
FIG. 11 is a plan view from beneath the same component.

The bearing components are in two halves, medial and lateral, a medial half 30 being shown in FIGS. 9, 10 and 11. This allows for different forms or heights of components to be used in the medial or lateral compartments, and also relates to the construction of the lateral meniscal type tibial baseplate 1 as set forth in the Applicants' U.S. Pat. No. 5,080,675. In this case the same fixed medial bearing elements are used in this total condylar design as are used in the lateral meniscal design.

The shape of the intercondylar eminence 23 is chosen to minimize incursion of this feature into the available bearing area of the bearing components so that the maximum thickness of the bearing material is available in the condylar area. Nevertheless, it is designed in such a way as to encompass the screw seating for the screw 60 for the modular stems 50 and so that at its posterior margin it encompasses the full width of the posterior cruciate cut out area in the tray. This again assists in reinforcing and strengthening this area, since it is the site of historical fracturing of metal tibial trays.

The posterior face 24 of the intercondylar eminence 23 is seen to be angled continuously at 30° in a conical form. This allows for the passage of the posterior cruciate ligament past this feature without the presence of sharp elements which could abrade against the soft tissue structure. This 30° cone surface is extended further onto the posterior surface of the intercondylar area of the bearing components 30 to match up on assembly, as is most clearly shown in FIG. 9 and indicated by reference numeral 25.

Two similar but opposite handed bearing components are used, a medial 30 and a lateral (not shown), or a left and a right component. These may be of varying heights and also of varying sectional or rotational forms as referred to above. The features on the under surface of each bearing component match the male features on the top of the baseplate 1. The elements are constructed in ultra high molecular weight polyethylene and a small catch 31 engages through the elasticity of the material with the lip 21 on the base plate. A further catch 32 is provided which engages beneath the hook retention 22.

The use of separate medial and lateral bearing components is, however, not essential, and in an alternative construction a stabilizer type bearing component which fits into the same trays as the separate medial and lateral components can be of one piece bearing construction. This engages the lip 21 on either the medial or lateral extreme of the tibial tray and then snap fits into the lip 31 on the opposite side of the component, clearing all the male features by having appropriate cut outs in its undersurface.

As shown in FIG. 1 the assembled tibial element comprises the tibial tray 1, bearing components 30 on its upper surface and a stem 50 which is drawn and locked into place by a fixing screw 60. Thus the element is assembled by inserting the stem into the bore 6 and locking it in place by the locking screw 60.

The tibial element is provided with a number of different modular stems for alternative use with the baseplate 1. The stem 50 shown in FIG. 1 is of known type and has a generally cylindrical form with grooves 51 for engagement either of cement or into bone tissue. This type of stem is provided in a number of different lengths and diameters so that they can be easily matched to the patients particular requirements. At the upper end of the stem there is a spigot 52 which has a male morse taper with a female screw thread 53 running internally into it.

In practice, the stem male taper is introduced into the female taper in the bore 6 of the tibial baseplate 1 and the fixing screw 60 is inserted into the thread 53 in the stem to draw the male taper into engagement with the female taper and retain it rigidly in place. A Nylock TM pellet (not shown) is used to ensure that this screw 60 does not loosen subsequently after implantation. In addition, the snapping into place of the bearing components or component will also avoid the danger of this screw becoming disconnected and floating into the patient's joint. There is no provision with this stem for locating it in a predetermined angular position relative to the tray.

Figure 6:
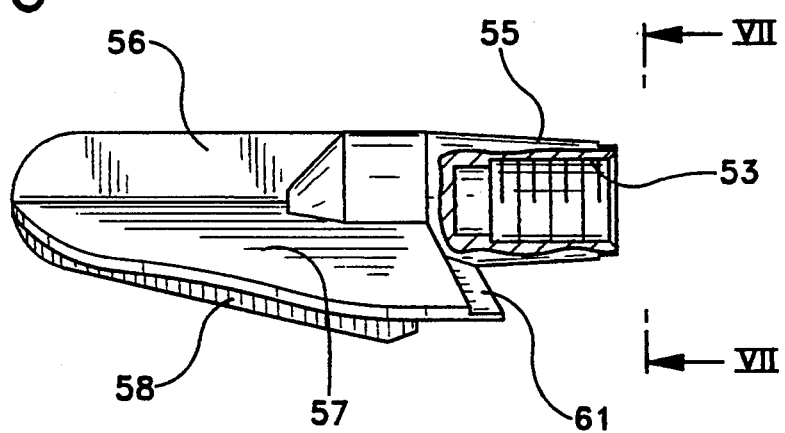
FIG. 6 is a part cross-sectional view of a shaped stem for use in the invention.
Figure 7:
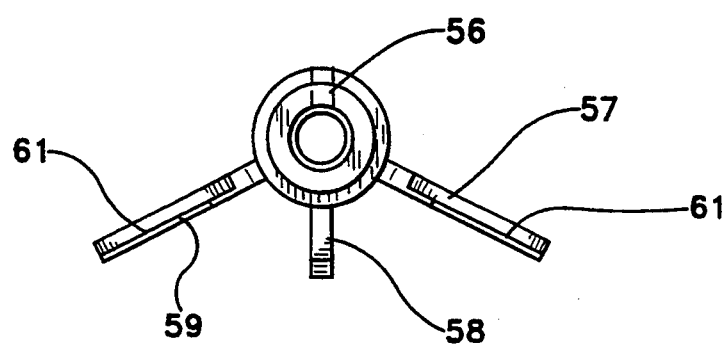
FIG. 7 is an end view in the direction of the arrow VII in FIG. 6.
Figure 8:
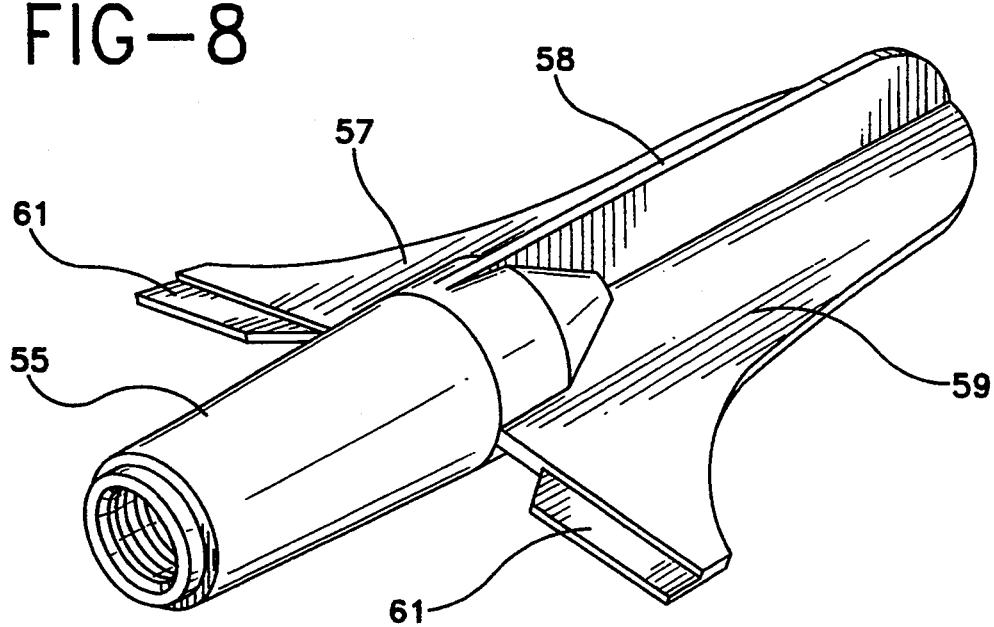
FIG. 8 is an isometric view of the stem shown in FIGS. 6 and 7.

An alternative form of stem is shown in FIGS. 6, 7 and 8 which embodies the invention. This stem comprises a spigot 55 of similar shape and configuration to the spigot 52 as shown in FIG. 1 and is provided with substantially radially outwardly projecting flanges in the form of four fins 56, 57, 58 and 59. The fins 57 and 59 match and line up with the fins 3 on the base plate 1.

Each of the fins 57 and 59 have location portions provided by protruding extensions 61 which, when the stem is in position, cooperate with the recesses 5 in the wings 3, thus locating the stem in a predetermined angular position and aligning it with the base plate 1. The locating means prevent relative angular movement between the part when the screw 60 is tightened.

The cruciform stem provides excellent resistance to torsion and also to medial lateral and anterior posterior bending loads exerted on the tray 1. Nevertheless, the finned form of the stem means that very little bone stock needs to be removed from the tibia to accommodate it.

Moreover, when stems of this type are used with the base plate described above, of either the cylindrical or cruciform type, the use of screws is not precluded because of the particular geometry chosen. In this respect, the screw shown in FIG. 12, because of its spherical head form and very low profile, allows it to be located within the thickness of the metal tibial tray 1, and for the screws angulation through cones of up to 30° included angle as per the surgeon's choice at intervention.

It will be appreciated that there can be many alternative stem shapes which can be used with benefit, provided they can be correctly aligned. The facility to use any one of a number of modular stems allows the surgeon to select the appropriate stem for the operation concerned.

When the product is delivered to the market place, the bore 6 of the tray can be blocked by a tapered plastic plug. If modular stems are to be used with the tray, this plug, which can be constructed from a number of different biocompatible plastics, can be punched out from the socket and the appropriate stem is interconnected in its place.

While several examples of the present invention have been described, it is obvious that many changes and modifications may be made thereunto, without departing from the spirit and scope of the invention.

We claim:

1. A tibial element for a replacement knee prosthesis comprising a tibial tray provided with at least one bearing component and a stem which can be attached to said tray by a tapered spigot and socket construction, said stem including at least two radially extending fins said tray having a lower portion including at least two radially extending fins intended for engagement with a proximal subcondylar area of the tibia, and means formed on said fin on said tray are included for engaging and locating said fin on said stem in a predetermined angular position in relation to said fins on the tray.

2. A tibial element as claimed in claim 1 wherein said locating means include contact elements formed on each of said fins on said tray and said stem which engage to create said predetermined angular position therebetween.

3. A tibial element as claimed in claim 2 wherein said at least two fins extend radially outwardly from the spigot and socket connection with a predetermined angle therebetween.

4. A tibial element as claimed in claim 3 wherein two of said abutments are provided, one on each of said fins, and at positions spaced radially away from the spigot and socket connection.

5. A tibial element as claimed in claim 1 wherein two of said flanges on said stem are spaced at the same predetermined angle as said radially outwardly extending fins on said tray.

6. A tibial element as claimed in claim 5 wherein said stem is of substantially cruciform cross-section to provide four radially extending wings.

7. A tibial element as claimed in claim 1 further including means for drawing the spigot and socket connection together and maintaining it in position.

8. A tibial element as claimed in claim 1 wherein the lower surface of the tray is provided with an ingrowth surface to allow bone to interlock therewith.

9. A tibial element as claimed in claim 1 further including openings in the tray to receive screws to secure the tray.

10. A prosthetic tibial component comprising:

a tibial tray having an underside for engaging a prepared tibial plateau, a stem having a tapered connection element at one end thereof, and said stem having at least two bone engagement elements in the form of radially extending fins for engaging said bone, said tray including a tapered connection element for mating with said tapered connection element on said stem, and said tray including at least two fins for engaging and locating a respective one of said at least two radially extending fins on said stem to locate said fins on said stem in a predetermined angular position in relation to said tibial plateau.

* * * * *